(12) United States Patent
Myrman

(10) Patent No.: US 6,668,826 B1
(45) Date of Patent: Dec. 30, 2003

(54) AIRBRAKE

(75) Inventor: Mattias Myrman, Stockholm (SE)

(73) Assignee: Microdrug AG, Hergiswil (CH)

( * ) Notice: Subject to any disclaimer, the term of this patent is extended or adjusted under 35 U.S.C. 154(b) by 0 days.

(21) Appl. No.: 09/690,018

(22) Filed: Oct. 17, 2000

(30) Foreign Application Priority Data

Sep. 25, 2000 (SE) .............................................. 0003411

(51) Int. Cl.⁷ .............................................. B65D 83/06
(52) U.S. Cl. ................ 128/203.15; 604/58; 128/203.12
(58) Field of Search ........................ 128/200.14–200.24, 128/203.12, 203.14, 203.15, 203.23, 203.24, 203.25, 203.28, 204.18, 204.28, 205.11, 205.13–205.18, 205.24, 207.14, 207.18; 604/58–62

(56) References Cited

U.S. PATENT DOCUMENTS 4,969,578 A * 11/1990 Gander et al. .............. 222/131
5,645,050 A * 7/1997 Zierenberg et al. ..... 128/203.15
5,727,546 A * 3/1998 Clarke et al. .......... 128/203.15
5,954,047 A * 9/1999 Armer et al. .......... 128/200.23

* cited by examiner

Primary Examiner—Glenn K. Dawson
(74) Attorney, Agent, or Firm—Young & Thompson

(57) ABSTRACT

A device is disclosed for controlling the duration of an administration of a prescribed dose of dry powder to a user's lung when inhaling the powder by use of a dry powder inhaler (DPI). The present device controls the speed of a moving cassette (4) carrying medical powder doses to one by one be administered by the DPI to a user. Generally the dose is pre-metered and applied to the cassette in the form of a strip (31) or a series of spots of ready-prepared powder. The present device using the airbrake arrangement (22) prolongs the time during which the pre-metered powder dose is released to the inhalation air. Adjustment means of the airbrake arrangement (22) define leakage of air (36) and thereby motion speed of a spring-loaded cassette (4). During the motion of the cassette the powder dose is sucked from the prepared dose powder strip onto the cassette (4) by a nozzle (1) connected to a mouthpiece used for inhaling medical powder from the dry powder inhaler.

22 Claims, 4 Drawing Sheets

AIRBRAKE

TECHNICAL FIELD

The present invention relates to a dry powder inhaler for administration of a medical dry powder to the lungs of a user, and more exactly to an airbrake device for prolonging the time for dose delivery upon inhalation.

BACKGROUND

Today supply and distribution of medical powders take place in many different ways. Within health care more and more is focussed on the possibility to dose and distribute powder directly to the lungs of a user by means of an inhaler to obtain an efficient, fast, and user friendly administration of the specific medical substance.

Inhalers have been developed from being very simple to the up-to-date relatively complicated devices. For the up-to-date inhalers some form of dosing process is almost entirely used for preparing the dose to be inhaled. Most often the dosing of the amount to be inhaled takes place industrially in advance in a dose package containing of the order 5–50 doses. The inhaler then is loaded with this dose package as the source of each dose. Other inhalers have a magazine from which the powder is dosed by some device for distribution to the inspiration air. In both cases the powder will generally be strongly agglomerated and therefore must be dispersed.

This dispersion of the agglomerates today mainly takes place by means of techniques in which the energy of the inspiration air is utilized. A normal inhalation takes place during about two seconds and a peaceful inspiration takes 3–4 seconds. In such designs, in which only the inhalation air is utilized for the de-agglomeration, only a fraction of the energy of the inhalation air will be utilized, as the dose of powder is given normally during only 0.1 to 0.4 s. Consequently this results in a low exploitation of the available energy which, as a matter of fact, will be present in the inhalation air. As only a small portion of the amount of energy is used it will be too low for a sufficient de-agglomeration to take place. The total respirable dose therefore becomes very dependent on the occasion and the individual user and thereby very varying from time to time. To improve this condition a number of inhalers include some kind of device against which the powder should collide and thereby transfer energy for de-agglomerating the powder. However, such a collision with a fixed or mechanically moving object involves that a relatively large amount of powder sticks either permanently or is transported further together with the next dose. In both cases this constitutes a negative factor for the goal of obtaining a high accuracy and quality of the inhaled dose, e.g. an accurate amount of powder having a high portion of very small particles.

In a document WO97/00704 is described an inhaler device in which the substance to be administered is charged electrostatically and the dosing is performed by means of the assistance of a rotating dosing drum attracting the charged particles of the substance. The substance is then emitted from the dosing drum by means of a combination of an additional electric field and the air stream resulting from an inspiration. In advance of a desired dosing step the substance to be administered is kept in a reservoir, loaded for instance by means of receiving a cartridge containing the substance intended for many operations of the device.

However here is still a demand for simple means for prolonging a dose delivery during an inhalation to obtain a full effectiveness of a pre-metered medical powder dose administered to a user's lung.

SUMMARY

The present invention discloses a device for controlling the duration of an administration of a prescribed dose of dry powder to a user's lung when inhaling the powder by means of a dry powder inhaler (DPI). The present device controls the speed and time characteristics of a moving cassette carrying medical powder doses to one by one be administered by the DPI to a user. Generally the dose is pre-metered and applied to the cassette in the form of a strip or a series of spots of ready-prepared powder. An airbrake device prolongs the time during which the pre-metered powder dose is released to the inhalation air. Adjustment means of the airbrake device define the motion speed of a motion of spring-loaded cassette during which the powder dose is sucked from the prepared dose powder strip onto the cassette by a nozzle connected to a mouthpiece.

A device for controlling dosing speed and timing of an inhaler device is set forth by the independent claim 1, and further embodiments are set forth by the dependent claims 2 to 7.

DESCRIPTION OF THE DRAWINGS

The invention will be described in the form of a preferred and illuminating embodiment and by means of the attached drawings wherein like reference numbers indicate like or corresponding elements and wherein.

DESCRIPTION OF THE INVENTION

When a user starts to inhale through the mouthpiece of the DPI, the cassette is released from its start position and begins to move propelled by a drive spring. In the preferred embodiment a compression spring is used, but it is equally possible to use a spring working in the expansion mode, indeed the force may come from other sources e.g. hydraulic or pneumatic. The cassette is carrying pre-metered doses preferably in the form of strips of powder. The powder preferably constitutes an electro-powder having well defined electrostatic properties as well as forming a major fine particle fraction with particles of a size preferably between 0.5 and 5 µm.

Figure 1:
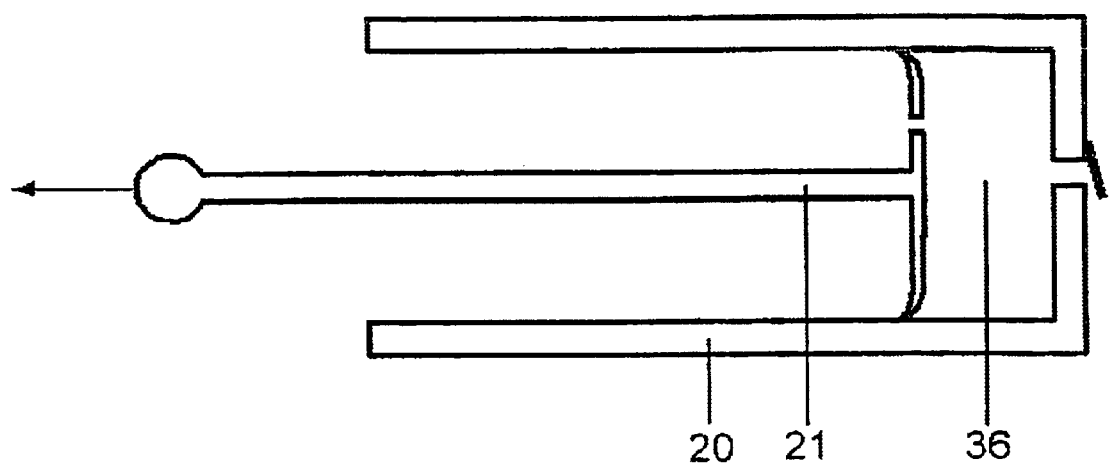
FIG. 1 illustrates a principal sketch of an airbrake in the form of a cylinder.
Figure 2:
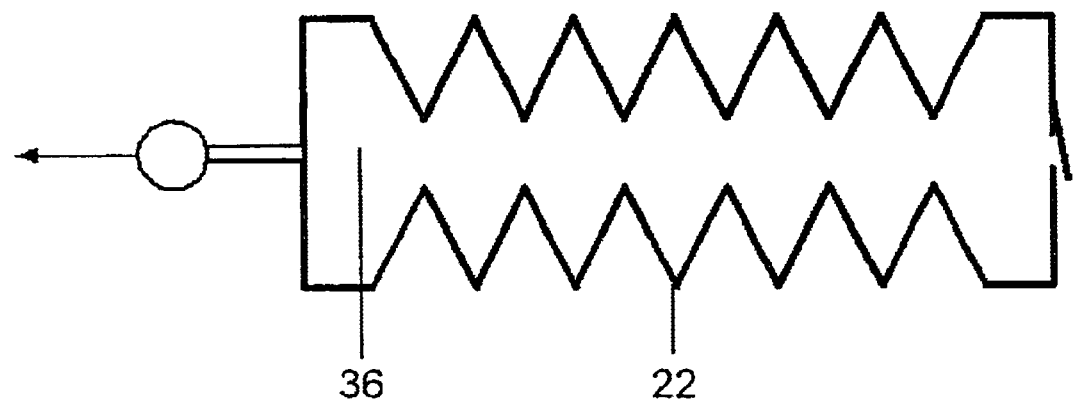
FIG. 2 illustrates another principal sketch of the airbrake in the form of bellows.
Figure 3:
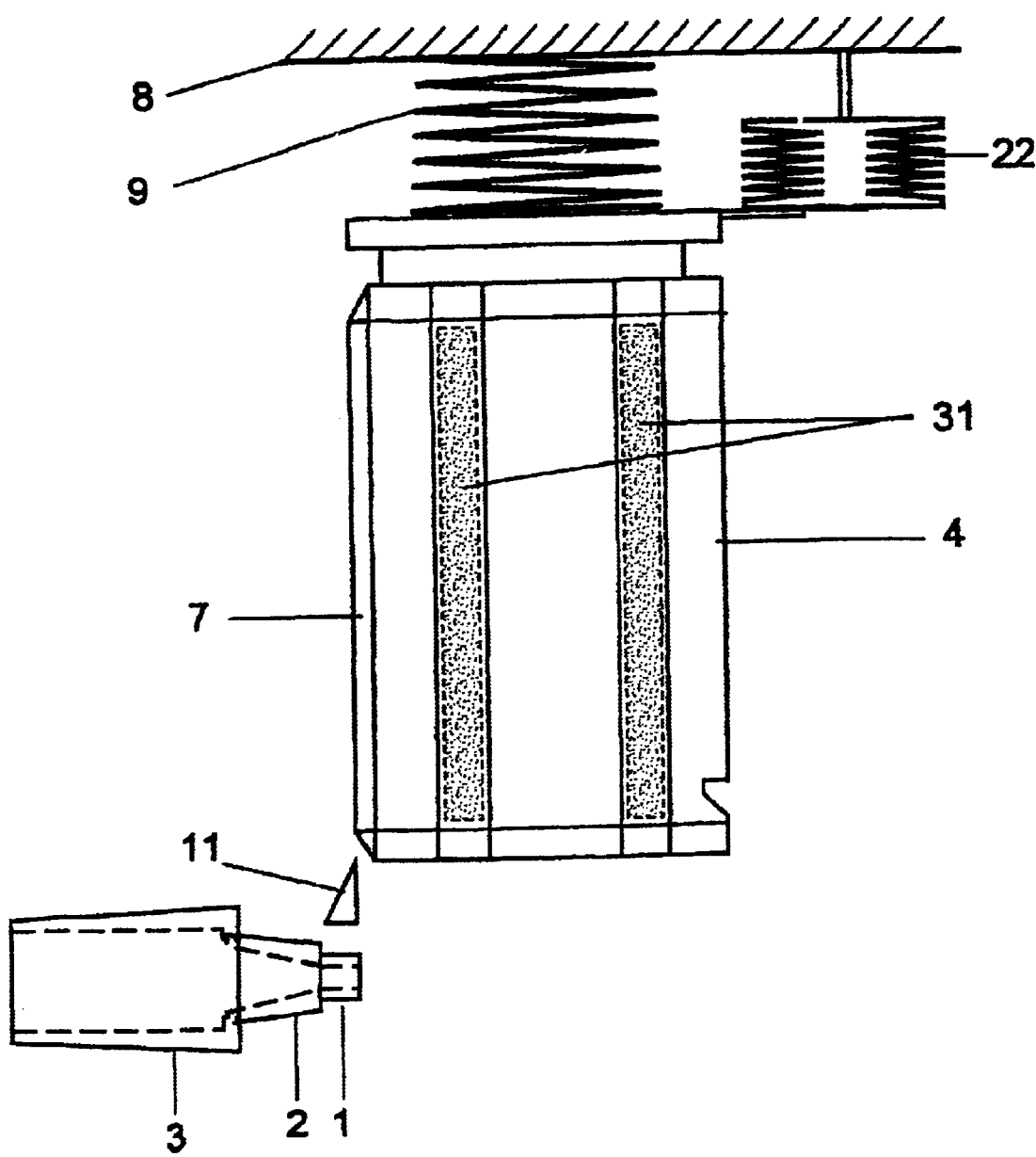
FIG. 3 illustrates a principal sketch of the internals of the inhaler with the airbrake illustrated in the form of a bellows and with the relevant parts in their respective positions prior to an inhalation by the user.
Figure 4:
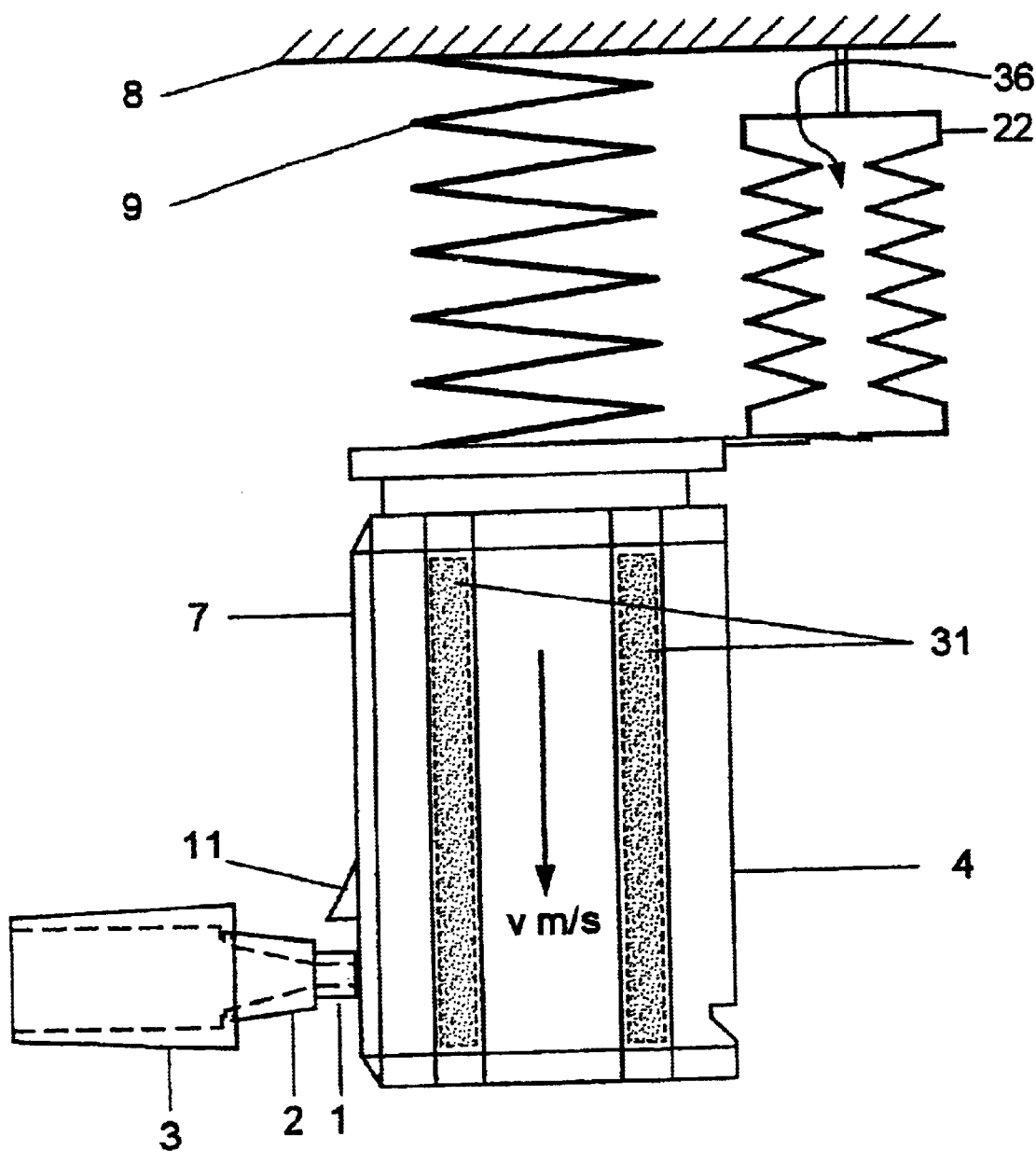
FIG. 4 illustrates a principal sketch of the internals of the inhaler with the airbrake illustrated in the form of a bellows and with the relevant parts in their respective positions shortly after the inhalation by the user has begun.

The device according to the present invention is coupled to the cassette carrying the prepared doses and acts as an airbrake, which controls in an administering process the speed and the timing of the moving cassette. The selected dose to be administered from the cassette is transported from the moving cassette via air sucked by means of a nozzle 1 of the suction tube 33, comprising besides the nozzle 1 a diffuser 2 and a porous tube 3, all of which fitted to the mouthpiece (FIG. 3). As the flow of inhaled air flows past the dose before going into the nozzle, the powder of the dose is sucked up and dispersed into this air for the length of time it will take for the dose onto the moving cassette to pass by the nozzle 1. Thus the airbrake controls the delivery of the dose. The delivery can be set from a high concentration in a short time to a low concentration in a long time and anything in between. A continuous administration of the dose is made possible Typically this time span is of the order of 0.2–4 seconds.

The object of designing and including an airbrake as an important part of a dry powder inhaler is to control the time during which the dose is delivered to the user. This is an important factor in achieving the overall goal of a continuous dose delivery to the user and in making a local or system delivery possible or a combination thereof. It is easy to adjust the speed and timing of the cassette and thereby the time it takes to administer the dose by increasing or decreasing the braking action of the airbrake device by changing one or more of its characteristics.

The airbrake device is preferably in the form of a variable volume of confined air, which is coupled to the DPI body 8 and the moving cassette 4. Preferably the airbrake is arranged such, that it is forced to expand or contract when the cassette 4 moves in relation to the body. In the preferred embodiment the confinement can be in the form of a bellows or a cylinder with a piston, but also other embodiments are possible. The continuous braking action, which controls the speed of the cassette 4 is achieved by letting air into or out of the airbrake device through a controlled leakage, e.g. through one or more holes connecting the variable volume with the surrounding atmosphere. In the case of cylinder with piston a small gap between the piston and the cylinder will be another possibility.

In FIGS. 1 and 2 are presented two illustrative embodiments of an airbrake device 22 enclosing a regulated volume of air 36 in accordance with the present invention.

For a better understanding of the mode of operation of the airbrake device only the vital internal parts of an inhaler are illustrated in an illustrative embodiment according to FIGS. 3, 4 and 5. The airbrake is illustrated as a bellows 22, but other embodiments of the airbrake are equally possible, e.g. a piston 21 and cylinder 20 arrangement as illustrated in FIG. 1, and this and all other alternative embodiments are included as accepted variations of the present invention. Those skilled in the art can no doubt see several possible ways of applying the airbrake in a DPI, but common to all cases is that one end of the airbrake is fixed directly or indirectly to the body 8 of the DPI and the other end is fixed directly or indirectly to a moving dose carrier, also referred to as the cassette 4. In FIG. 3 are shown the relative positions of the vital internal parts of the DPI in the loaded state prior to an inhalation by the user. For the sake of simplicity, the illustrations of FIGS. 3, 4 and 5 show the cassette member in the form of a cylinder carrying doses 31 arranged on the cylindrical surface in rectangular beds with the long axis parallel to the axis of the cassette. The motion of the cassette while delivering the dose is normally in a straight line along the longitudinal axis, but alternatively a rotation around the axis or a combination of rotation and linear motion will be possible, depending on the geometry of the dose distribution on the cassette member.

FIG. 4 shows the cassette shortly after beginning to inhale, the inhalation releasing the cassette from its loaded ready-to-go state by means of a release mechanism that is not part of the present invention and not illustrated in the figures. The cassette 4 is propelled forward by the drive spring 9 with a speed determined by the force of the spring 9 and the braking action of the air brake 22. The airbrake 22 then is forced to expand as the cassette moves forward.

Assuming a zero pressure difference between the surrounding atmosphere and the internal volume of the air brake device and provided there is no leakage of air between the surrounding atmosphere and the internal volume of the air brake device, the braking power increases with the distance of travel for the cassette. The reason being that the internal volume of the airbrake is forced to increase as the cassette moves forward, which increases the induced vacuum in the then enlarged but enclosed volume of the airbrake device. This increasing difference in pressure between the internal vacuum and the external atmospheric pressure results in an increasing force, the braking force, which tries to push the airbrake back to its original size. At a certain distance of travel the counteracting forces of the drive spring 9 and the air brake 22 balance each other exactly and the cassette cannot move further.

By introducing a small controlled amount of leakage from the surrounding air to the internal air 36 volume of the airbrake the vacuum and consequently the braking force will be reduced with time and allowing the cassette to move forward along its path of motion with a controlled speed.

Further the effects of a disturbance of the cassette movement arising for example by some mechanical imperfection or wear have to be accounted for. In these cases the airbrake will automatically help to keep the speed constant, because as the disturbance tries to slow down the moving cassette the braking action by the airbrake is simultaneously reduced, which increases the drive force of the spring that tries to overcome the disturbance.

The air thus leaking into the airbrake arrangement is taken from filtered air inside the DPI body, eliminating the risk of dirty air clogging the aperture or apertures leaking air into the airbrake arrangement. Since the speed of the cassette is controlled such that it is repeatable from one dose to the next and if the geometry of the pre-metered dose strip is the same for all doses, the time to deliver a dose will be constant.

In another embodiment of the invention it is possible to arrange the air brake device such that the internal volume is forced to contract rather than expand by the moving cassette, creating an over pressure instead of vacuum, but otherwise completely analogue to the principle of operation described in the foregoing.

To minimize the power needed from the user to close the inhaler when pushing the cover to the closed position, which tightens the drive spring and forces the airbrake back to its original size, the airbrake has an additional air inlet with a check valve or similar arrangement, which lets air into or out of the variable volume, whichever the case may be, so that the loading operation by the user is made as easy as possible.

Also illustrated in FIG. 4 is a foil cutter 11 cutting open an aluminum foil (not shown) that seals the recess 7 of the cassette surface for protecting the underlying dose 31 on the dose bed in order to make a selected dose accessible to the air stream upon an inhalation. The cutter is in a fixed position such that when the cassette is pushed past the cutter it cuts through the foil and opens it up just before the nozzle 1, which is part of the suction tube consisting of a nozzle 1, a diffuser 2 and a porous tube 3. Next the dose on the dose bed reaches the point where the nozzle is positioned and as the cassette is pushed past the nozzle, the inhaled air sucks up and disperses the powder of the dose in the stream of air and delivers the dose to the user for the pre-set amount of time.

Figure 5:
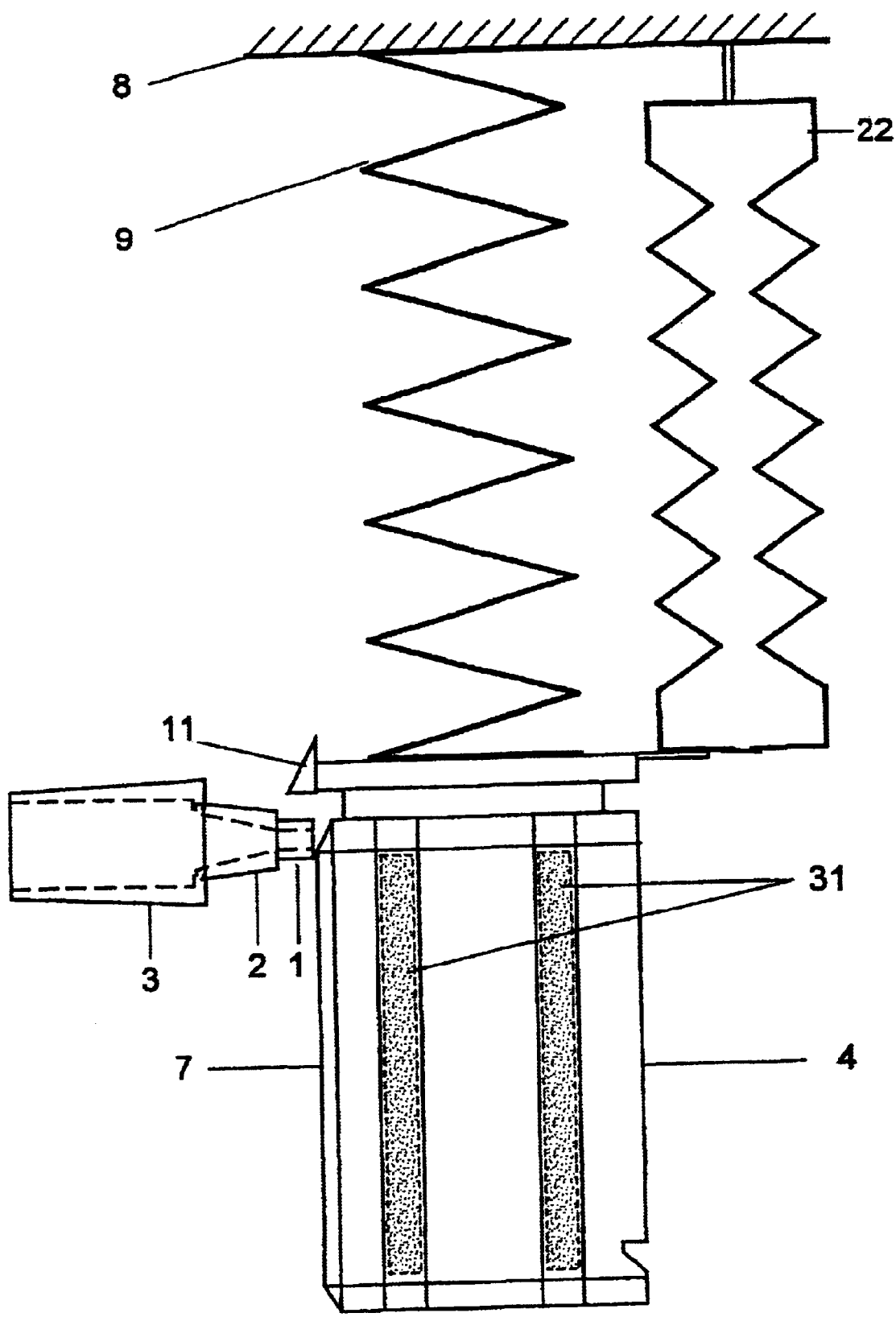
FIG. 5 illustrates a principal sketch of the internals of the inhaler with the airbrake illustrated in the form of a bellows and with the relevant parts in their respective positions when the inhalation by the user has ended.

In FIG. 5 the cassette has reached the end of its travel, the dosing is completed and the full dose has been delivered to the user.

Particularly the present invention will be of great interest in the design of a new continuous inhaler, which thereby will present a number of advantages in comparison to prior art inhalers found on the market today and which commonly deliver a dose during a very short period of time, often of the order 0.2 to 0.3 seconds.

The present invention has been described by means of an illustrative embodiment for disclosing its operation, but it will be apparent to a person skilled in the art, that there may be performed numerous modification and changes to the present invention without departure from the object and scope thereof, which are defined by the appended claims

What is claimed is:

1. A braking device controlling a time of release of powder from a dry powder inhaler comprising:
    a dose carrier to be put in motion during an inhalation;
    a first force element; and
    a device member enclosing a volume of air comprising an arrangement for letting out or letting in air into said device member at a selected rate;
    wherein the first force element and the device member are arranged so that, a first force exerted by this first force element causes a motion of the dose carrier and a change in the enclosed volume of air in the device member, causing a change of pressure inside the device member, thereby forming a second force counteracting the first force.

2. The device according to claim 1, wherein said device member comprises a cylinder with a piston provided with the arrangement for controlling leakage of air into or out of the enclosed volume.

3. The device according to claim 2, wherein the first force element comprises a spring, the spring providing the exerted first force that is applied to an end surface of said dose carrier.

4. The device according to claim 3, wherein said spring is a compression spring.

5. The device according to claim 3, wherein said device member and the spring are arranged so that each comes into close proximity of a same end surface of said dose carrier.

6. The device according to claim 3, wherein adjustment of said arrangement for controlling a leakage of air changes a rate of the change in the enclosed volume of air in the device member.

7. The device according to claim 3, wherein said device member and the spring are arranged so that each comes into contact with a same end surface of said dose carrier.

8. The device according to claim 2, wherein said arrangement for letting in or letting out air of said device member comprises a check valve.

9. The device according to claim 1, wherein said device member comprises a bellows provided with the arrangement for controlling a leakage of air into or out of the enclosed volume.

10. The device according to claim 9, wherein the first force element comprises a spring, the spring providing the exerted first force for application to an end surface of said dose carrier.

11. The device according to claim 10, wherein said spring is a compression spring.

12. The device according to claim 10, wherein said device member and the spring are arranged so that each comes into close proximity of a same end surface of said dose carrier.

13. The device according to claim 10, wherein adjustment of said arrangement for controlling a leakage of air changes a rate of the change in the enclosed volume of air in the device member.

14. The device according to claim 10, wherein said device member and the spring are arranged so that each comes into contact with a same end surface of said dose carrier.

15. The device according to claim 9, wherein said arrangement for letting in or letting out air of said device member comprises a check valve.

16. An inhaler device containing a braking device, comprising:
    a body;
    a movable dose carrier installed in the device;
    an adjustable volume chamber attached to the body, the adjustable volume chamber comprising a passage connecting an interior and an exterior of the chamber; and
    a source of a first force connected between the body and the adjustable volume chamber;
    wherein the first force bears on the moving dose carrier, and wherein when the moving dose carrier is moved with respect to the body by the first force, the volume of the adjustable volume chamber is changed.

17. The inhaler device of claim 16, wherein the change of the volume of the adjustable volume chamber causes a resistance to the first force as air is moved between the interior and the exterior of the adjustable volume chamber through the passage.

18. The inhaler device of claim 17, wherein the source of the first force comprises a spring.

19. The inhaler device of claim 17, wherein the adjustable volume chamber comprises a cylinder and a piston arranged within the cylinder.

20. The inhaler device of claim 17, wherein the adjustable volume chamber comprises a bellows.

21. The inhaler device of claim 17, wherein the adjustable volume chamber comprises a check valve, so that passage of the air in a first direction between the interior and the exterior of the chamber is resisted less than passage of the air in a second direction opposite the first direction.

22. An inhaler with an installed dose carrier, comprising:
    a body;
    a dose carrier installed inside the body;
    a means for providing a first force between the dose carrier and the body;
    an adjustable volume chamber connected to the body and the dose carrier, so that when the dose carrier is released from an initial position, the dose carrier moves with respect to the body and a volume of the adjustable volume chamber is changed, causing resistance to the movement of the dose carrier.

* * * * *